(12) United States Patent
Berg et al.

(10) Patent No.: US 8,420,153 B2
(45) Date of Patent: Apr. 16, 2013

(54) COATING WITH ANTIMICROBIAL AGENTS

(75) Inventors: Eric P. Berg, Grapevine, TX (US); Rita Stella, Cambourne (GB)

(73) Assignee: Mentor Worldwide LLC, Santa Barbara, CA (US)

(*) Notice: Subject to any disclaimer, the term of this patent is extended or adjusted under 35 U.S.C. 154(b) by 88 days.

(21) Appl. No.: 12/233,949

(22) Filed: Sep. 19, 2008

(65) Prior Publication Data

US 2010/0076113 A1 Mar. 25, 2010

(51) Int. Cl.
*A61L 31/10* (2006.01)
*B32B 27/06* (2006.01)
*B05D 1/00* (2006.01)
*A61F 2/12* (2006.01)

(52) U.S. Cl.
USPC ............... 427/2.24; 428/447; 523/113; 623/8

(58) Field of Classification Search .................... 523/113
See application file for complete search history.

(56) References Cited

U.S. PATENT DOCUMENTS

| | | | | |
|---|---|---|---|---|
| 3,279,996 A * | 10/1966 | Long, Jr. et al. | ............... | 424/424 |
| 3,366,975 A * | 2/1968 | Pangman | ............... | 623/8 |
| 3,598,123 A * | 8/1971 | Zaffaroni | ............... | 424/435 |
| 3,920,805 A * | 11/1975 | Roseman | ............... | 424/432 |
| 4,012,497 A | 3/1977 | Schopflin | | |
| 4,191,741 A * | 3/1980 | Hudson et al. | ............... | 424/425 |
| 4,230,686 A * | 10/1980 | Schopflin et al. | ............... | 424/425 |
| 4,292,965 A * | 10/1981 | Nash et al. | ............... | 128/833 |
| 4,455,691 A * | 6/1984 | Van Aken Redinger et al. | . | 623/8 |
| 4,479,795 A * | 10/1984 | Mustacich et al. | ............... | 604/500 |
| 4,511,620 A * | 4/1985 | Kroupa et al. | ............... | 428/220 |
| 4,648,880 A * | 3/1987 | Brauman | ............... | 623/8 |
| 4,650,487 A * | 3/1987 | Chaglassian | ............... | 623/8 |
| 4,713,073 A * | 12/1987 | Reinmuller | ............... | 623/8 |
| 4,822,616 A * | 4/1989 | Zimmermann et al. | ............... | 424/432 |
| 4,889,744 A * | 12/1989 | Quaid | ............... | 427/2.24 |
| 4,952,419 A * | 8/1990 | De Leon et al. | ............... | 427/2.14 |
| 4,960,425 A * | 10/1990 | Yan et al. | ............... | 623/8 |
| 4,985,253 A * | 1/1991 | Fujioka et al. | ............... | 424/488 |
| 4,992,312 A * | 2/1991 | Frisch | ............... | 428/35.7 |
| 5,019,096 A * | 5/1991 | Fox et al. | ............... | 600/36 |
| 5,141,748 A * | 8/1992 | Rizzo | ............... | 424/425 |
| 5,217,493 A | 6/1993 | Raad et al. | | |
| 5,376,117 A | 12/1994 | Pinchuk et al. | | |
| 5,624,704 A | 4/1997 | Darouiche et al. | | |
| 5,674,285 A * | 10/1997 | Quaid | ............... | 623/8 |
| 5,788,980 A * | 8/1998 | Nabahi | ............... | 424/430 |
| 5,879,697 A * | 3/1999 | Ding et al. | ............... | 424/422 |
| 5,902,283 A | 5/1999 | Darouiche et al. | | |
| 5,961,552 A * | 10/1999 | Iversen et al. | ............... | 623/8 |
| 5,972,372 A * | 10/1999 | Saleh et al. | ............... | 424/432 |
| 6,039,968 A * | 3/2000 | Nabahi | ............... | 424/433 |
| 6,103,256 A * | 8/2000 | Nabahi | ............... | 424/430 |
| 6,224,579 B1 | 5/2001 | Modak et al. | | |
| 6,436,422 B1 | 8/2002 | Trogolo et al. | | |
| 6,913,626 B2 * | 7/2005 | McGhan | ............... | 623/23.73 |
| 6,951,654 B2 * | 10/2005 | Malcolm et al. | ............... | 424/430 |
| 7,097,690 B2 | 8/2006 | Usher et al. | | |
| 7,625,405 B2 * | 12/2009 | Purkait | ............... | 623/8 |
| 7,658,727 B1 * | 2/2010 | Fernandes et al. | ............... | 604/265 |
| 2003/0044451 A1 | 3/2003 | McGhee et al. | | |
| 2004/0039349 A1 | 2/2004 | Modak et al. | | |
| 2004/0116551 A1 * | 6/2004 | Terry | ............... | 523/122 |
| 2005/0079365 A1 | 4/2005 | Widenhouse et al. | | |
| 2005/0186246 A1 | 8/2005 | Hunter et al. | | |
| 2006/0165751 A1 * | 7/2006 | Chudzik et al. | ............... | 424/422 |
| 2008/0241212 A1 * | 10/2008 | Moses et al. | ............... | 424/423 |
| 2009/0198333 A1 | 8/2009 | Becker | | |

FOREIGN PATENT DOCUMENTS

| WO | WO 2005/072281 | 8/2005 |
|---|---|---|
| WO | WO 2008/121816 | 10/2008 |
| WO | WO 2010/033656 | 3/2010 |

OTHER PUBLICATIONS

Darouiche Rabi O et al. "In vivo efficacy of antimicrobe-impregnated saline-filled silicone implants" Plastic and Reconstructive Surgery, 2002, 1352-1357.*

Encyclopedia of Polymer Science and Engineering, vol. 15, 1989, pp. 204-308 plus to cover pages.*

Darouiche Rabih O et al: "In vivo efficacy of antimicrobe-impregnated saline-filled silicone implants" Plastic and Reconstructive Surgery, Williams and Wilkins Co., Baltimore, MD, US, 2002.

PCT Search Report dated Dec. 29, 2009 from PCT application No. PCT/US2009/057243 as issued by the European Patent Office as searching authority.

* cited by examiner

*Primary Examiner* — Robert S Loewe

(57) ABSTRACT

A coating with antimicrobial agents for use with medical devices. In one approach, a related method involves coating high temperature vulcanized silicone material with a room temperature vulcanized dispersion.

14 Claims, No Drawings

COATING WITH ANTIMICROBIAL AGENTS

BACKGROUND

The present disclosure is directed towards coatings, and more particularly towards a coating including antimicrobial agents for use in medical applications.

There has been research conducted in the area of coatings incorporating antimicrobial agents. Certain of the research has been directed towards coatings involving active release strategies. Antibiotics, silver ions, and antiseptics, have been among the antimicrobial agents studied.

In the area of antimicrobial coatings for medical devices, whether for short term use or long term permanent implants, many scientific publications refer to their use in connection with central venous catheters, urinary tract catheters and penile prostheses. A particular combination of two antibiotics, Rifampin and Minocycline, has been shown to successfully reduce biofilm colonization on these specific devices.

A number of methods to coat silicone surfaces of medical devices have also been previously studied. In one known approach, impregnation of a device with antibiotics dissolved in a swelling agent was employed. In other approaches, coatings involved application of a film of silicone oil followed by antimicrobial agents in a powder form or a graft-polymerization of a coating incorporating a drug. In yet another approach, a hydrophilic polymer containing antibiotic ceramic particles was utilized.

Many of these methods and approaches can be classified as "surface coatings" since only the surface of the device is coated by antibiotics. However, another method designed to promote the penetration of the antimicrobial agents throughout the volume of the device ("impregnation") is also known.

These methods and other related approaches published in the literature or reported in patents can suffer from a number of limitations. In some cases, the coating is superficial ("surface coating"), thereby providing only a short time of effective protection against bacteria following the initial burst release of the active drug. Moreover, when the "impregnation" method is used, the advantage of an extended period of antimicrobial efficacy is achieved by incorporating the drug into the volume of the device by swelling the material forming the device (for example silicone) and subsequently physically trapping the active substance within. However, this often requires a large amount of drug, most of which will not become available at the surface and will remain in the bulk of the device given the high affinity of the drugs for the device material. Also, swelling finished devices to incorporate drugs may have undesired effects on their mechanical properties or it may introduce unwanted volatile residues within the composition (for example a gel). This is particularly true with long term or permanent prostheses such as breast implants.

Accordingly, there is a need for a coating with an antimicrobial agent that can be used in connection with a medical device while providing extended effective protection without requiring a large amount of drugs to accomplish desired protection. The present disclosure addresses these and other needs.

SUMMARY

Briefly and in general terms, the present disclosure is directed towards a method and related substance for coating material. More specifically, the present disclosure is directed towards coating material with a dispersion incorporating antimicrobial agents. In one particular aspect, the approach involves coating high temperature vulcanized (HTV) silicone material with a room temperature vulcanized (RTV) dispersion incorporating antimicrobial agents for use in medical implants.

In one embodiment, an approach involves incorporating a combination of active drugs into a RTV silicone elastomer dispersion and coating a previously cured HTV elastomer material with the dispersion. Although various drugs can be employed, Rifampin and Minocycline are among contemplated active ingredients. Application of the drug loaded RTV dispersion to the HTV material can be done by dipping, spraying, painting or other physical deposition or conventional methods. The thickness of the coating can be accurately controlled to obtain a precise amount of active drugs in the silicone. The coated material can then be cured under controlled temperature and humidity conditions. The antimicrobial agents are therefore incorporated into the most external layer of the silicone shell of the device.

Other features and advantages will become apparent from the following detailed description, taken in conjunction with the accompanying drawings, which illustrate by way of example, the features of the various embodiments.

DETAILED DESCRIPTION

The present disclosure addresses the need for a coating containing antimicrobial agents for use with medical devices. The coating provides extended effective protection without requiring a large amount of drugs to accomplish a protective objective.

The present approach involves incorporating active drugs directly into a silicone matrix without swelling the material forming the subject device. In this way, the drugs can be distributed within an outermost RTV part of a silicone shell for longer term efficacy but are not wasted in the whole volume of the material in large quantity as is common with a conventional "impregnation" approach. The thickness of the RTV layer can be controlled precisely to achieve the desired concentration volume distribution of the drugs. This is made possible due to an innovative use of a combination of RTV silicone elastomer containing antimicrobial drugs cured onto a HTV elastomer substrate.

The present approach to coating provides long term efficacy of the antimicrobial protection as the drugs are incorporated into the silicone matrix in comparison with those methods where drugs are present only on the surface of the device. Moreover, the contemplated method allows use of a much lower concentration of drugs in comparison with impregnation methods, thereby minimizing the cost of materials while maintaining the same antimicrobial efficacy. Accordingly, the disclosed method makes it possible to accurately control the amount of drugs incorporated and the thickness of the coatings in order to optimize the release kinetics and customize the concentration needed for a specific application.

Significantly, the present coating procedure does not introduce any substantial mechanical stress to the finished device following swelling of the material. Further, the approach does not introduce solvents into the gel of the finished device which may require further processing to extract volatiles and it is compatible with a variety of physical coating techniques such as spray and dipping, greatly simplifying the manufacturing process.

One preferred embodiment of the subject coating method involves forming an antimicrobial composition, of an effective concentration to prevent bacterial colonization of a medical device surface. As stated, it is contemplated that Rifampin and Minocycline can be employed as active ingredients. The antimicrobial agents are then dissolved or finely dispersed in organic solvents. Organic solvents which can be used include acetic acid and xylene.

Next, the antimicrobial solutions (or antimicrobial dispersions) are incorporated into an uncured RTV silicone elastomer dispersion. The mixture is heated and stirred until each solution (or dispersion) is uniformly incorporated within the silicone dispersion.

In an application specific to medical devices, the dispersion including the antimicrobial agents is applied onto the surface of a target medical device made of already cured HTV silicone elastomer. Spraying the dispersion onto the medical device can be used in the application process. Thereafter, the coated device is cured for a period of about 60 to 180 minutes at a temperature of 90° to 200° F. until the dispersion incorporating the antimicrobial agents is fully cured.

In one specific example, 100 mg of Rifampin can be dispersed in a 2 ml of Xylene on a hotplate at 80° C. under stirring conditions. A quantity of 50 mg of Minocycline can then be dissolved in 0.5 ml of Acetic Acid on a hotplate at 80° C. under stirring conditions for 15 minutes. A 1 g quantity of RTV silicone dispersion is then slowly added to the Minocycline solution and stirred for a few minutes. The mixture of Minocycline and RTV dispersion is then added to 19 g of RTV silicone dispersion under stirring conditions.

Subsequently, the Rifampin dispersion is added to the mixture under stirring conditions. The mixture is to be stirred on the hotplate at 80° C. until a honey consistency of uniform appearance and color is reached. The mixture can be filmed onto a cured shell of HTV silicone material using spraying or other conventional methods.

It is to be recognized that the above described method can involve using any other desired combination of antibiotics, antifungal substances or antiseptic agents. Moreover, it is to be appreciated that the method can involve employing organic solvents other than Acetic Acid and Xylene. Further, the method can include coating the dispersion onto the HTV material by physical coating methods, i.e. dipping or spraying. One application of this approach is for breast implants but it is to be recognized that the disclosed approach has applicability to other areas of art.

The various embodiments described above are provided by way of illustration only and should not be construed to limit the disclosed embodiments. Those skilled in the art will readily recognize various modifications and changes that may be made to the disclosed embodiments without following the example embodiments and applications illustrated and described herein, and without departing from the true spirit and scope of the disclosed embodiments, which is set forth in the following claims.

What is claimed is:

1. A method for coating a material with active drugs, comprising:
    incorporating an active drug into a first material of silicone elastomer that is uncured;
    stirring the active drug and the first material of silicone elastomer at 80° C. until a uniform color and uniform consistency is reached;
    forming a coating composition including the active drug and the uncured material;
    applying the coating composition to a second cured material of silicone elastomer, wherein the first material is the most external layer, and without swelling the cured silicone elastomer material.

2. The method of claim 1, wherein the first uncured material is an uncured RTV silicone elastomer.

3. The method of claim 2, wherein the second material is a cured HTV silicone elastomer.

4. The method of claim 1, wherein the active drug is one or more of Rifampin and Minocycline.

5. The method of claim 1, comprising coating in an amount to provide an effective concentration to prevent bacterial colonization.

6. The method of claim 5, comprising coating a medical device.

7. The method of claim 6, comprising coating a portion of a breast implant.

8. The method of claim 6, comprising incorporating the active drug into an external layer of a silicone elastomer sheath of the device.

9. The method of claim 1, comprising dissolving or dispersing the active drug into an organic solvent to form an antimicrobial solution or dispersion.

10. The method of claim 9, wherein the organic solvent is one or more of acetic acid and xylene.

11. The method of claim 9, comprising incorporating the antimicrobial solution or dispersion into an uncured RTV silicone elastomer dispersion to form a mixture.

12. The method of claim 11, comprising applying the mixture onto cured HTV silicone elastomer surface of the device.

13. The method of claim 12, comprising curing the uncured silicone elastomer.

14. The method of claim 13, comprising curing for about 60 to 180 minutes at a temperature of 90 to 200 degrees Fahrenheit.

* * * * *